US008835673B2

(12) United States Patent
Mattke et al.

(10) Patent No.: US 8,835,673 B2
(45) Date of Patent: Sep. 16, 2014

(54) PROCESS FOR PREPARING ISOCYANATES

(75) Inventors: Torsten Mattke, Freinsheim (DE);
Eckhard Stroefer, Mannheim (DE);
Julia Leschinski, Mannheim (DE);
Radwan Abdallah, Ludwigshafen (DE);
Axel Franzke, Mannheim (DE);
Michael Bock, Ruppertsberg (DE)

(73) Assignee: BASF SE, Ludwigshafen (DE)

( * ) Notice: Subject to any disclaimer, the term of this patent is extended or adjusted under 35 U.S.C. 154(b) by 268 days.

(21) Appl. No.: 13/513,595

(22) PCT Filed: Dec. 3, 2010

(86) PCT No.: PCT/EP2010/068811
§ 371 (c)(1),
(2), (4) Date: Jun. 4, 2012

(87) PCT Pub. No.: WO2011/067369
PCT Pub. Date: Jun. 9, 2011

(65) Prior Publication Data
US 2012/0253063 A1    Oct. 4, 2012

(30) Foreign Application Priority Data
Dec. 4, 2009  (EP) ..................... 09178079

(51) Int. Cl.
*C07C 263/04* (2006.01)
(52) U.S. Cl.
CPC .................................. *C07C 263/04* (2013.01)
USPC .......................................... 560/338; 560/345
(58) Field of Classification Search
CPC ................................................... C07C 263/04
USPC .......................................................... 560/345
See application file for complete search history.

(56) References Cited

U.S. PATENT DOCUMENTS

| | | | | |
|---|---|---|---|---|
| 4,207,251 | A * | 6/1980 | Heyboer .................. | 560/338 |
| 5,155,267 | A | 10/1992 | Faraj | |
| 5,686,645 | A | 11/1997 | Faraj | |
| 6,433,219 | B1 | 8/2002 | Stroefer et al. | |
| 6,781,010 | B1 | 8/2004 | Mason | |
| 2011/0015446 | A1 | 1/2011 | Mäurer et al. | |
| 2011/0105785 | A1 | 5/2011 | Knoesche et al. | |
| 2011/0207961 | A1 | 8/2011 | Geissler et al. | |
| 2011/0213178 | A1 | 9/2011 | Mattke et al. | |
| 2011/0251425 | A1 | 10/2011 | Penzel et al. | |
| 2011/0257428 | A1 | 10/2011 | Knoesche et al. | |
| 2011/0263892 | A1 | 10/2011 | Breuninger et al. | |
| 2011/0301380 | A1 | 12/2011 | Knoesche et al. | |
| 2011/0313192 | A1 | 12/2011 | Rosendahl et al. | |
| 2012/0004445 | A1 | 1/2012 | Lehr et al. | |
| 2012/0004446 | A1 | 1/2012 | Mattke et al. | |
| 2012/0016154 | A1 | 1/2012 | Mattke et al. | |
| 2012/0101299 | A1 | 4/2012 | Schelling et al. | |
| 2012/0108843 | A1 | 5/2012 | Schelling et al. | |
| 2012/0123151 | A1 | 5/2012 | Bock et al. | |
| 2012/0123153 | A1 | 5/2012 | Bock et al. | |
| 2012/0142960 | A1 | 6/2012 | Bock et al. | |

FOREIGN PATENT DOCUMENTS

| | | |
|---|---|---|
| CN | 1850792 | 10/2006 |
| DE | 198 55 959 | 6/2000 |
| DE | 199 07 648 | 8/2000 |
| EP | 0 018 588 | 11/1980 |
| EP | 0 027 952 | 5/1981 |
| EP | 0 028 338 | 5/1981 |
| EP | 0 028 724 | 5/1981 |
| EP | 0 030 039 | 6/1981 |
| EP | 0 100 047 | 2/1984 |
| EP | 0 123 412 | 10/1984 |
| EP | 0 126 299 | 11/1984 |
| EP | 0 092 738 | 7/1985 |
| EP | 0 566 925 | 10/1993 |
| EP | 0 555 628 | 5/1996 |
| EP | 0 795 543 | 10/2001 |
| EP | 1 160 239 | 12/2001 |
| EP | 1 259 480 | 11/2002 |
| EP | 1 270 544 | 1/2003 |
| EP | 1 616 857 | 1/2006 |
| EP | 1 449 826 | 12/2008 |
| WO | 02 24634 | 3/2002 |
| WO | 2004 056756 | 7/2004 |
| WO | 2006 130405 | 12/2006 |
| WO | 2006 131381 | 12/2006 |
| WO | 2008 006775 | 1/2008 |
| WO | 2008 025659 | 3/2008 |
| WO | 2008 049783 | 5/2008 |
| WO | 2009 115492 | 9/2009 |

OTHER PUBLICATIONS

U.S. Appl. No. 13/587,378, filed Aug. 16, 2012, Mattke, et al.
U.S. Appl. No. 13/687,670, Nov. 28, 2012, Mattke, et al.
Leardini, R., et al., "A New and Facile Synthesis of Alkyl N-Arylcarbamates," Communications, vol. 3, pp. 225-227, (Mar. 1982).
Siefken, W., "Mono- und Polyisocyanate," Justus Liebigs Annalen Der Chemie, vol. 562, No. 75, pp. 76-136, (1949).
Chen, D., et al., "Catalytic Decomposition of Methylene Di (Phenylene Carbamate) by ZnO," Chinese Journal of Catalysis, vol. 26, No. 11, pp. 987-992, (Nov. 2005) (with English abstract).
Wegefahrt, R.F., "Oxidehydrierung von Formamiden, Ein chlorfreies Verfahren zur Isocyanatsynthese," Dissertation, Uni zu Koeln, pp. 1-96, (Feb. 9, 2000).

(Continued)

*Primary Examiner* — Yong Chu
(74) *Attorney, Agent, or Firm* — Oblon, Spivak, McClelland, Maier & Neustadt, L.L.P.

(57) ABSTRACT

Process for preparing aromatic isocyanates by reacting the corresponding formamides with an oxygen-comprising gas over noble metal catalysts at temperatures of from 300 to 600° C. and a contact time of from 1 to 1000 ms, wherein:
  a. the formamide is vaporized before entering the reaction zone,
  b. the reaction mixture obtained is quenched with an alcohol-comprising quenching liquid and
  c. the urethane formed is dissociated into isocyanate and alcohol.

18 Claims, No Drawings

(56) References Cited

OTHER PUBLICATIONS

International Search Report Issued Mar. 7, 2011 in PCT/EP10/68811 Filed Dec. 3, 2010.

U.S. Appl. No. 13/434,135, Mar. 29, 2012, Lehr, et al.
U.S. Appl. No. 13/479,961, May 24, 2012, Stroefer, et al.
U.S. Appl. No. 13/661,652, Oct. 26, 2012, Leschinski, et al.

* cited by examiner

PROCESS FOR PREPARING ISOCYANATES

The present invention relates to a novel process for preparing isocyanates.

Isocyanates, in particular diisocyanates, are valuable basic chemicals for the production of polyurethanes. Polyurethanes are the class of polymers having the widest uses in various applications. Accordingly, the world markets for diisocyanates and polyurethanes have displayed high growth rates over some years. The most important isocyanates are MDI (methylenedi(phenyl isocyanate)), TDI (tolylene diisocyanate) and PMDI (polymeric methylenedi(phenyl isocyanate)).

The TDI process firstly gives a mixture comprising predominantly isomers of TDI and oligomers which are crosslinked via urea and diisocyanate groups. The composition of the oligomers is determined by the production process. The pure isomers or isomer mixtures are generally obtained from the crude TDI mixture by a distillative separation step. Preferred isomer mixtures are those of 2,4- and 2,6-TDI in a molar ratio of from 80:20 to 60:40.

It is known that isocyanates can be prepared from amines and phosgene. Depending on the type of amines, the reaction is carried out either in the gas phase or the liquid phase and batchwise or continuously (W. Siefken; Liebig Annalen der Chemie 562, 75 (1949)). The continuous preparation of organic diisocyanates by reaction of primary organic amines and phosgene has been described many times and is routine on an industrial scale (Ullmanns Enzyklopädie der technischen Chemie, Volume 7, Third Edition, Carl Hanser Verlag, p. 76 ff. (1993)).

Modern-day industrial syntheses of isocyanates are carried out virtually exclusively in continuous processes. In general, the continuous embodiment of the process has a number of stages. In the first stage of the phosgenation, the amine is reacted with phosgene to form the corresponding carbamoyl chloride and hydrogen chloride and hence amine hydrochlorides.

The primary reaction between amines and phosgene is very fast and exothermic. To minimize the formation of by-products and solids, amine and phosgene, if appropriate both dissolved in an organic solvent, are mixed quickly. The next stage of the phosgenation comprises both the decomposition of the carbamoyl chloride into the desired isocyanate and hydrogen chloride and also the phosgenation of the amine hydrochloride to form the carbamoyl chloride. Liquid-phase phosgenations are described, for example, in EP-A 1 616 857, WO 2004/056756, WO 2006/130405 and EP-A 012 70 544. To avoid formation of amine hydrochlorides, which are undesirable intermediates, the phosgenation can also be carried out as a gas-phase phosgenation at elevated temperatures. Processes are described, for example, in EP-B 1 449 826 and WO 2008006775 (aerosol phosgenation). Phosgenations in the supercritical region have also been described (WO 2008/049783).

A critical disadvantage of the above-described processes is the use of phosgene which is highly toxic for human beings and the environment. Plants in which phosgene is processed therefore have to have comprehensive, costly safety precautions and facilities and also have to meet strict legal requirements.

Phosgene-free processes have already been employed for small amounts of specific diisocyanates (EP-A 18588, EP-A 27952, EP-A 126299, EP-A 566925). In the case of aromatic diisocyanates which are produced in large amounts, possible phosgene-free routes have been discussed in the literature but have hitherto not been implemented (WO 2006/131381, EP-A 1 259 480, EP-A 1 160 239, EP-A 28338, Chinese Journal of Catalysis Vol. 26 No. 11 (2005), 987-992, CN-A-1850792). Mention may here be made by way of example of the reductive carbonylation of nitro compounds, the oxidative carbonylation of amines, the carboalkoxylation or carboaroxylation of amines and also the synthesis and subsequent dissociation of carbamates (WO 2008/025659 A1; Six and Richter: Isocyanates, Organic in Ullmanns Enzyklopädie der technischen Chemie, Volume 7, Carl Hanser Verlag).

The oxydehydrogenation of formamides has also been described in the literature. Wegefahrt (thesis by Ralf Wegefahrt, University of Cologne, 2000) describes the oxydehydrogenation of monomethylformamide by means of an oxygen/helium mixture over a silver catalyst. After the reaction, the exiting reaction mixture is quickly cooled to RT by means of a quench with water or ethanol. To determine the reaction conversion quantitatively, the volatile methyl isocyanate formed is collected in the form of N,N'-dimethylurea by addition of methylamine. Collection of the methyl isocyanate as urethane by means of ethanol was not employed because of the lower reaction rate.

The oxydehydrogenation of aliphatic and aromatic formamides over various noble metals is described in U.S. Pat. No. 4,207,251. The formamides are reacted in gaseous form in the presence of oxygen at from 300 to 600° C. to form the corresponding isocyanates. The reaction mixture is then, if appropriate after prior cooling, brought into contact with a water-immiscible, high-boiling solvent (boiling point >150° C., preferably from 200 to 300° C.) for the isocyanate to separate off water formed. The yield of tolylene 2,4-diisocyanate is low at 27% since the formamide is partly or completely oxidized to $CO_2$ and water or partly to completely decarbonylated to the amine. The amines which arise in this way then form high-boiling ureas with the isocyanates formed and these ureas would have to be redissociated with a high consumption of energy.

The disadvantages of the phosgene-free processes described are the high specific capital costs and also the low selectivity and thus total yield compared to conventional variants using phosgene. The reasons for the low yield are undesirable parallel reactions such as oxidation or decarbonylation. Thus, these routes are both economically (costs) and ecologically (more residues and by-products) unfavorable and in need of improvement.

It is therefore an object of the present invention to develop an improved phosgene-free process for preparing aromatic isocyanates, which does not have the abovementioned disadvantages and in particular the undesirable urea formation.

The invention accordingly provides a process for preparing aromatic isocyanates by reacting the corresponding formamides with an oxygen-comprising gas over noble metal catalysts at temperatures of from 300 to 600° C. and a contact time of from 1 to 1000 ms, wherein:

a. the formamide is vaporized before entering the reaction zone,
b. the reaction mixture obtained is quenched with an alcohol-comprising quenching liquid and
c. the urethane formed is dissociated into isocyanate and alcohol.

The formamides used are monocyclic or polycyclic aromatic monoformamides, bisformamides or polyformamides which are N-monosubstituted. The formamides correspond to the general formula $R(NH-CHO)_n$, where R is an optionally substituted $C_6$-$C_{24}$-aryl radical, preferably $C_6$-$C_{18}$-aryl radical, in particular $C_6$-$C_{10}$-aryl radical and particularly preferably phenyl, and n is an integer from 1 to 3, preferably 1 or 2, per aromatic ring. Suitable substituents are, for example, chlorine, fluorine, cyano, alkyl, alkoxy, alkylcarbonyl and/or alkoxycarbonyl, where alkyl and alkoxy generally have from 1 to 10, preferably from 1 to 6, particularly preferably from 1 to 4, carbon atoms. Preference is given to phenylformamide (=formanilide) and toluenebisformamide, with particular preference being given to 2,4- and 2,6-toluenebisformamide.

The formamides corresponding to the desired isocyanate are vaporized by stripping or atomization with the gaseous starting materials or a hot inert gas and/or oxygen gas stream by means of a helical tube vaporizer, by means of a microstructured or millistructured vaporizer, by means of a falling film evaporator or a thin film evaporator or by spraying onto a hot vaporizer bed before they enter the reaction zone. The formamides are preferably continuously melted and transported as melt to the vaporizer.

The residence time during vaporization is 1-1000 ms, preferably from 10 to 400 ms.

The formamide is introduced in gaseous form into the reactor where the reaction with the oxygen-comprising gas takes place over a noble metal catalyst, with this catalyst being able to be used as a fixed bed in a tube reactor or else as a fluidized bed in a fluidized-bed reactor.

Noble metal catalysts suitable for the process are, in particular, those comprising the metals Cu, Au, Ag, Re, Pd, Pt, Rh, Ru, W or Os or mixtures thereof. Particular preference is given to catalysts comprising Cu and/or Ag as noble metal catalysts. Very particular preference is given to using silver catalysts. Furthermore, the noble metal catalyst can be provided with suitable foreign atoms such as Cu, Ag, Au, Re, Pd and/or Pt as dopants (=promoters). Preference is given to using catalysts composed of silver and promoters such as Cu, Au, Re, Pd and/or Pt.

The abovementioned noble metal catalysts can be employed with or without support material. In the case of the unsupported catalysts, advantageous results have been achieved using silver crystals and in particular silver wool.

As support material, preference is given to using a basic or acidic support material which is preferably composed of steatite, aluminum oxide, aluminosilicate, minerals from the group consisting of hydrotalcites or mixtures thereof. A particularly preferred support material is steatite, viz. a ceramic material which is based on natural raw materials and comprises the main component soapstone ($Mg(Si_4O_{10})(OH)_2$), a natural magnesium silicate. The support can also comprise additions of clay and feldspar or barium carbonate.

In the case of the supported noble metal-comprising catalysts, particularly advantageous results where achieved when it was applied to a support material by application of a complexed sparingly soluble compound of the noble metal, if appropriate in admixture with additives acting as promoters, from suspension or solution and the product obtained was subsequently treated thermally at temperatures in the range from 100 to 400° C. for a period of from 5 min to 5 h.

As a result of this thermal treatment, the noble metal itself is formed from the noble metal compound on the surface of the support material and this then represents the active species of the supported catalyst.

The noble metal contents, measured in % by weight and based on the support material, are generally in the range from 0.1 to 40% by weight, preferably in the range from 0.5 to 20% by weight and particularly preferably in the range from 1 to 10% by weight.

The promoter content is generally in the range from 0 to 1000 ppm by weight, based on the support material.

The use of silver oxalate as sparingly soluble noble metal compound is preferred, with the prior in-situ preparation of the oxalate being particularly preferred. A process of this type for producing a supported noble metal-comprising catalyst is described in the patent application PCT/EP2009/053081, which is not a prior publication.

In the process of the invention, the residence time of the reactants in the catalytically active zone is generally from 1 to 1000 ms, preferably from 100 to 400 ms. The temperature is generally from 300 to 600° C., preferably from 350 to 450° C.

According to the invention, an inert gas (e.g. nitrogen, carbon dioxide) is mixed into one or more of the reactants. The oxygen-comprising gas preferably comprises an excess of inert gas. In general, the proportion of oxygen in the oxygen-comprising gas is from 0.1 to 100% by volume, preferably 0.1-1% by volume, relative to an inert gas.

The local molar ratio of oxygen to formamide ($n_{O2}/n_{FA}$) is generally 0.1-20, in particular 0.5-5.

In an embodiment of the process of the invention, at least one reactant is added at the inlet to the reactor and at least one other reactant is added shortly before the catalyst bed. Thus, for example, the oxygen-comprising gas can be metered in together with the introduction of formamide at the beginning of the tube reactor or else only shortly before the catalyst bed in order to ensure a relatively short contact of the formamide with the oxygen.

In another embodiment of the process of the invention, at least one reactant is added at the inlet to the reactor and at least one other reactant is added at a plurality of places distributed over the length or height of the reactor. Thus, for example, the introduction of the oxygen-comprising gas can be distributed over various places on the reactor in order to avoid large local excesses of oxygen and the associated combustion of hydrocarbons. If the reaction zone of the process of the invention is configured as a catalytic fluidized bed comprising catalyst particles and, if appropriate, inert particles, this embodiment corresponds to addition distributed over the height of the fluidized bed.

Fluidization of the fluidized bed can be effected by the oxygen-comprising gas and/or an inert gas.

After flowing through the catalyst bed or the fluidized bed, the reaction gases are quickly and intensively mixed by direct contact with an alcohol-comprising quenching liquid so that the mixture cools to such an extent that the high-boiling reaction products and the remaining starting material condense out and isocyanate groups formed react with the alcohol to give the corresponding urethane. It is possible to inject or spray the quenching liquid by means of any customary systems (e.g. Venturi scrubbers) or introduce the reaction gases into the quenching liquid (e.g. in a bubble column). In principle, all apparatuses and concepts which allow intensive contact between gas phase and liquid phase are conceivable.

The molar ratio of quenching liquid to formamide is generally 1-10 000, preferably 10-1000.

As a result of quenching, the mixture of reaction products and quenching liquid formed should have a temperature significantly below the boiling point of the quenching liquid used. In general, the temperature of the reaction mixture should be from 40 to 80° C. below the boiling point of the quenching liquid in order to prevent reaction products and relatively large amounts of quenching liquid from leaving the quench via the gas phase.

The quenching liquid is at least one aliphatic or aromatic monoalcohol or polyalcohol having from 1 to 10 carbon atoms; this can be used either alone or in admixture with at least one aprotic dipolar solvent. The alcohol is preferably an aliphatic $C_1$-$C_6$-alcohol such as methanol, ethanol, n-propanol or isopropanol, n-butanol, isobutanol and/or tert-butanol, in particular isobutanol.

The alcohol or the alcoholic mixture should be present in a distinct excess over the isocyanates formed. The molar ratio of alcohol to isocyanate is preferably >5, particularly preferably >50. The aprotic dipolar solvent used for the alcoholic mixture is preferably a primary and/or secondary amide such as dimethylformamide or dimethylacetamide. The molar ratio of this solvent to the alcohol is preferably 0-20, particularly preferably 0.25-5.

The offgases obtained in the quenching operation and any low boilers comprised therein are preferably cooled to room temperature and can subsequently be recycled to the process, in which case a purge stream should be provided in order to discharge the gaseous reaction products.

The liquid products are separated (e.g. rectification) after the quenching stage and incompletely reacted formamides can be recirculated to the reaction stage. The alcohol used for the quenching operation and any solvent also used are likewise separated off and can be recirculated to the quenching stage.

After the quenching operation, the isocyanate corresponding to the urethane formed can be liberated by dissociation of the urethane, and the alcohol liberated at the same time can be recirculated to the process. Such a dissociation of urethane for the synthesis of isocyanates is known, for example, from DE-A-19855959 and is preferably carried out thermally at from 200 to 600° C., preferably from 250 to 450° C., and pressures of usually from 1 mbar to 1.5 bar, preferably from 1 mbar to 1 bar. The dissociation of the urethane can be carried out using, inter alia, columns (EP 0795543 B1), fluidized-bed reactors (EP 555 628 B1, DE 19907648 A1), falling film or thin-film evaporators (EP 0 092 738 B1). The dissociation can be carried out in the liquid phase or in the gas phase (EP 100047 A1, EP 0 028 724 A1).

In a particular embodiment, the N-arylurethane formed after the quenching process can be subjected to coupling with formaldehyde, resulting in formation of relatively high molecular weight methylene-linked N-arylurethanes, before the urethane dissociation. The coupling of N-arylurethanes with formaldehyde is known (EP-A 0 123 412, EP-A-0030039, U.S. Pat. No. B 6,433,219, H.-G- Franck and J. W. Stadelhofer: Industrielle Aromatenchemie, Springer-Verlag, 1987). Thus, for example, N-phenylurethane is reacted with formaldehyde in the presence of a catalyst based on a strong acid such as $H_2SO_4$, BF, trifluoroacetic acid, HCl in an aromatic solvent such as benzene, nitrobenzene at temperatures of from 70 to 100° C. The work-up to give the reaction product is carried out by conventional methods. Polymeric methylenedi(aryl isocyanate), e.g. PMDI, can then be obtained from the resulting product by means of the above-described urethane dissociation. The corresponding diarylmethane diisocyanates can subsequently be obtained therefrom in the desired purity by distillation. The preparation of PMDI and the diphenylmethane diisocyanates obtained therefrom is of particular industrial importance.

EXAMPLES

Production of the Supported Catalysts (Examples 3 and 4):
Steatite spheres having a diameter of from 1.6 to 2.2 mm (manufacturer: CeramTec) were wetted by application of a solution of silver oxalate and copper oxalate complexed by ethylenediamine. The steatite spheres wetted in this way with the silver-copper solution were subsequently treated at 280° C. in a stream of air for 12 minutes. The noble metal loading of the catalyst after coating is indicated in the respective examples.

Example 1

In a tube reactor, 13 ml/h of toluenebisformamide (TBF) melt were continuously vaporized at 455° C. together with nitrogen as inert gas in a fused silica bed, reacted with oxygen over 100 g of silver wool and subsequently cooled to 35° C. by means of 3.5 l/h of quenching liquid comprising 80% by mass of dimethylacetamide and 20% by mass of isobutanol. The residence time in the catalyst bed was 307 ms at a molar excess of oxygen ($n_{O2}/n_{TBF}$) of 11.

33 mol % of the TBF were completely oxidized. The conversion of TBF into aromatic products was 98 mol %, and the selectivity to the isocyanate group (without total oxidation) was 55 mol %.

Example 2

In a tube reactor, 6 ml/h of toluenebisformamide melt were continuously vaporized at 425° C. together with nitrogen as inert gas in a fused silica bed, reacted with oxygen over 100 g of silver wool and subsequently cooled to 35° C. by means of 3.5 l/h of quenching liquid comprising 20% by mass of dimethylacetamide and 80% by mass of isobutanol. The residence time in the catalyst bed was 245 ms at a molar excess of oxygen ($n_{O2}/n_{TBF}$) of 4.

7 mol % of the TBF were completely oxidized. The conversion of TBF was 97 mol %, and the selectivity to the isocyanate group (without total oxidation) was 74 mol %.

Example 3

In a tube reactor, 7.7 ml/h of toluenebisformamide melt were continuously vaporized at 400° C. together with nitrogen as inert gas in a fused silica bed, reacted with oxygen over 80 g of silver on steatite (12% by weight of Ag) and subsequently cooled to 35° C. by means of 3.5 l/h of quenching liquid comprising 20% by mass of dimethylacetamide and 80% by mass of isobutanol. The residence time in the catalyst bed was 332 ms at a molar excess of oxygen ($n_{O2}/n_{TBF}$) of 3.5 mol % of the TBF were completely oxidized. The conversion of TBF was 75 mol %, and the selectivity to the isocyanate group (without total oxidation) was 60 mol %.

Example 4

In a tube reactor, 10 ml/h of toluenebisformamide melt were continuously vaporized at 450° C. together with nitrogen as inert gas in a fused silica bed, reacted with oxygen over 80 g of silver (9.1% by weight)/Cu (150 ppm by weight) on steatite and subsequently cooled to 35° C. by means of 3.5 l/h of quenching liquid comprising 20% by mass of dimethylacetamide and 80% by mass of isobutanol. The residence time in the catalyst bed was 310 ms at a molar excess of oxygen ($n_{O2}/n_{TBF}$) of 13.57 mol % of the TBF were completely oxidized. The conversion of TBF was 91 mol %, and the selectivity to the isocyanate group (without total oxidation) was 72 mol %.

Example 5

In a tube reactor, 27 g/h of formanilide were continuously vaporized at 400° C. together with $CO_2$ as inert gas, reacted with oxygen over 30 g of silver wool and subsequently cooled to 35° C. with quenching liquid comprising 100% by mass of isobutanol. The residence time in the catalyst bed was 230 ms at a molar excess of oxygen ($n_{O2}/n_{TBF}$) of 0.37. The formanilide conversion was 50 mol % and the selectivity to the isocyanate group was 97 mol %.

The invention claimed is:

1. A process for preparing an aromatic isocyanate, comprising:
   vaporizing a corresponding formamide outside of a reaction zone, to obtain a vaporized corresponding formamide,
   reacting the vaporized corresponding formamide with an oxygen-comprising gas over a noble metal catalyst in the reaction zone at a temperature of from 300 to 600° C. and a contact time of from 1 to 1000 ms, to obtain a reaction mixture,
   quenching the reaction mixture with an alcohol-comprising quenching liquid, to obtain a urethane, and
   dissociating the urethane into isocyanate and alcohol.

2. The process of claim 1, wherein the formamide is a monocyclic or polycyclic aromatic monoformamide, bisformamide, or polyformamide.

3. The process of claim 1,
   wherein the noble metal catalyst is a silver catalyst consisting of pure silver or a silver-comprising mixed catalyst, and
   the noble metal catalyst is unsupported or is with support.

4. The process of claim 1, wherein an alcohol of the alcohol-comprising quenching liquid is an aliphatic or aromatic monoalcohol or polyalcohol having a chain length of $C_1$-$C_{10}$.

5. The process of claim 4, wherein the alcohol-comprising quenching liquid further comprises an aprotic dipolar solvent.

6. The process of claim 1, wherein a molar ratio of quenching liquid to formamide is from 1 to 10 000.

7. The process of claim 1, wherein the quenching comprises spraying, atomizing, or passing the reaction gas into the quenching liquid.

8. The process of claim 1, wherein a mixture of reaction product and quenching liquid has a temperature significantly below a boiling point of the quenching liquid.

9. The process of claim 1, further comprising:
   mechanically, thermally, or both mechanically and thermally separating a liquid product solution from the quenching liquid, the formamide, and the urethane, and
   subsequently recirculating the quenching liquid, the formamide, the urethane, or a combination thereof.

10. The process of claim 1, wherein the dissociating the urethane comprises dissociating the urethane thermally at a temperature of from 200 to 600° C. and a pressure of from 1 mbar to 1.5 bar.

11. The process of claim 1, further comprising:
   coupling an N-arylurethane with formaldehyde to obtain a relatively high molecular weight methylene-linked N-arylurethane, after the quenching and before the dissociating.

12. The process of claim 3, wherein the noble metal catalyst is a silver catalyst consisting of pure silver.

13. The process of claim 3, wherein the noble metal catalyst is a mixed catalyst comprising silver.

14. The process of claim 3, wherein the noble metal catalyst is unsupported.

15. The process of claim 14, wherein the noble metal catalyst is silver crystals or silver wool.

16. The process of claim 3, wherein the noble metal catalyst is with support.

17. The process of claim 6, wherein the molar ratio is from 10 to 1000.

18. The process of claim 1, wherein the contact time is from 10 to 400 ms.

* * * * *